United States Patent [19]

Grossmann et al.

[11] Patent Number: 4,999,041
[45] Date of Patent: Mar. 12, 1991

[54] USE OF DIPHENYL ETHER DERIVATIVES FOR THE DESICCATION AND ABSCISSION OF PLANT ORGANS

[75] Inventors: Klaus Grossmann, Limburgerhof, Fed. Rep. of Germany; Helmut Walter, Greenville, Miss.; Bruno Wuerzer, Otterstadt, Fed. Rep. of Germany

[73] Assignee: BASF Aktiengesellschaft, Ludwigshafen, Fed. Rep. of Germany

[21] Appl. No.: 452,108

[22] Filed: Dec. 18, 1989

[30] Foreign Application Priority Data

Aug. 7, 1989 [DE] Fed. Rep. of Germany ....... 3926055

[51] Int. Cl.$^5$ ...................... A01N 33/22; A01N 37/38
[52] U.S. Cl. ............................................. 71/70; 71/116
[58] Field of Search ..................................... 71/70, 116

[56] References Cited

U.S. PATENT DOCUMENTS

| 3,798,276 | 3/1974 | Bayer et al. | 260/612 R |
| 4,285,723 | 8/1981 | Cartwright et al. | 71/103 |
| 4,304,936 | 12/1981 | Rohr et al. | 71/70 |
| 4,460,399 | 7/1984 | Chan | 71/70 |

FOREIGN PATENT DOCUMENTS

| 0001427 | 4/1979 | European Pat. Off. |
| 0208245 | 4/1989 | European Pat. Off. |
| 2076393 | 12/1981 | United Kingdom |

OTHER PUBLICATIONS

Chem. Abstracts, vol. 91, 1979, 15125, "The Effect of Buthidazole & New Diphenyl Other . . . ", Dalem et al.

Primary Examiner—Glennon H. Hollrah
Assistant Examiner—Brian Burn
Attorney, Agent, or Firm—Keil & Weinkauf

[57] ABSTRACT

The use of diphenyl ether derivatives of the general formula I

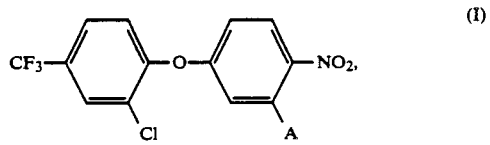

where A is a radical

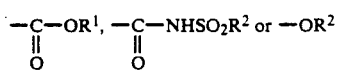

where $R^1$ is hydrogen, an alkali metal or alkaline earth metal ion, substituted or unsubstituted ammonium, alkyl of from 1 to 4 carbon atoms or alkoxycarbonylalkyl of a total of 1 to 6 carbon atoms and $R^2$ is alkyl of from 1 to 4 carbon atoms, for the desiccation and abscission of plant organs.

3 Claims, No Drawings

USE OF DIPHENYL ETHER DERIVATIVES FOR THE DESICCATION AND ABSCISSION OF PLANT ORGANS

The present invention relates to the use of diphenyl ether derivatives of the general formula I

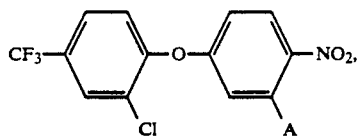

where A is a radical

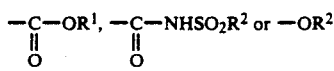

where $R^1$ is hydrogen, an alkali metal or alkaline earth metal ion, substituted or unsubstituted ammonium, alkyl of from 1 to 4 carbon atoms or alkoxycarbonylalkyl of a total of 1 to 6 carbon atoms and $R^2$ is alkyl of from 1 to 4 carbon atoms, for the desiccation and abscission of plant organs, especially for defoliating cotton.

The invention further relates to a process for the desiccation and abscission of plant organs, especially the leaves, by means of the above compounds I.

EP-A-00 01 427 discloses that a specific substituted diphenyl ether, viz., 2,6-dichloro-3'-fluoro-4-trifluoromethyl-6'-nitrodiphenyl ether, has a desiccating and defoliant action in cotton plants.

The use of specifically substituted diphenyl ethers as herbicides has been disclosed in a number of publications. DE-A-23 11 638 and EP-A-00 40 898 may be mentioned by way of example, where the active ingredients 5-[2-chloro-4-(trifluoromethyl)-phenoxy]-2-nitrobenzoic acid and its salts (Blazer ®, common name: acifluorfen) and 5-[2-chloro-4-(trifluoromethyl)-phenoxy]-2-nitrobenzoic acid-(ethoxycarbonylmethyl)-ester (Superblazer ®) are listed.

EP-A-3416 describes the herbicidal action of 5-[2-chloro-4-(trifluoromethyl)-phenoxy]-N-(methylsulfonyl)-2-nitrobenzamide. The compounds 5-[2-chloro-4-(trifluoromethyl)-phenoxy]-2-nitrobenzoic acid-(ethoxycarbonyleth-2-yl)-ester and 2-chloro-1-(3-ethoxy-4-nitrophenoxy)-4-(trifluoromethyl)-benzene are known under their common names lactofen and oxyfluorfen.

Mixtures of diphenyl ether derivatives I in which A is $COOR^1$ with quinoline derivatives for regulating plant growth are disclosed in EP-A-208 245 (DE-A-35 24 319).

There is considerable economic interest in abscissants and desiccating agents because they facilitate harvesting. Particularly in intensive cotton farming, the use of defoliants is a basic prerequisite for the effective utilization of strippers for harvesting. The commercial products used hitherto do not meet essential practical requirements such as rapid and lasting action even at cool temperatures, low application rates and low burden on the environment (toxicity, odor, combustibility).

It was therefore the object of the invention to provide active ingredients useful for abscission, in particular systematically inducing leaves, blossoms or fruit to drop, e.g., in crop plants such as cotton, citruses, olives, and pomes and drupes, and as desiccants for drying out the visible parts of crop plants such as potatoes, rape, sunflowers and soybeans.

We have now found that the diphenyl ethers defined at the outset have a pronounced action with regard to the abscission and desiccation of plant organs. They offer, compared with prior art agents, considerable advantages:

(a) at comparable application rates, their action is much more comprehensive;

(b) they have a much surer action even at low temperatures.

In addition to their excellent action as defoliants, particularly for defoliating cotton, the compounds I have a very good action when used as desiccants for drying out the visible parts of crop plants such as potatoes, sunflowers, soybeans and rape so as to facilitate harvesting.

In compounds I, $R^1$ is especially hydrogen, sodium, ethoxycarbonylmethyl or ethoxycarbonyleth-2-yl. Instead of the acid when $R^1=H$, the corresponding alkali metal, ammonium or alkaline earth metal salts may be used. Examples of alkali metal salts are lithium, sodium and potassium salts. Examples of alkaline earth metals salts are magnesium and calcium salts. In the case of ammonium salts, $R^1$ is for example the unsubstituted ammonium ion, and ammonium ions in which 1, 2 or all 3 hydrogen atoms are replaced by substituents such as straight-chain or branched alkyl radicals of from 1 to 4 carbon atoms and which are unsubstituted or substituted by halogen (Cl, Br), hydroxy or $C_1$-$C_4$-alkoxy, or in which two of the alkyl radicals are linked to each other to form a five-membered or six-membered ring which may contain a further hetero-atom such as oxygen or sulfur.

$R^1$ may also denote $C_1$-$C_4$-alkyl such as methyl, ethyl, propyl, isopropyl or butyl, or $C_1$-$C_6$-alkoxycarbonylalkyl, e.g., $C_1$-$C_3$-alkoxycarbonyl-$C_1$-$C_2$-alkyl such as methoxycarbonylmethyl, methoxycarbonylethyl, ethoxycarbonylethyl, propoxycarbonylmethyl and especially ethoxycarbonylmethyl and ethoxycarbonyleth-2-yl.

$R^2$ denotes $C_1$-$C_4$-alkyl such as methyl, ethyl, propyl or butyl, especially methyl and ethyl.

The following diphenyl ether derivatives are given by way of example:

| No. | Structure | Common name |
|---|---|---|
| 1 | CF$_3$—⟨⟩—O—⟨⟩—NO$_2$ with Cl and COOH | acifluorfen |
| 2 | CF$_3$—⟨⟩—O—⟨⟩—NO$_2$ with Cl and COO⊖Na⊕ | acifluorfen-sodium |
| 3 | CF$_3$—⟨⟩—O—⟨⟩—NO$_2$ with Cl and COO⊖NH$_4$⊕ | |
| 4 | CF$_3$—⟨⟩—O—⟨⟩—NO$_2$ with Cl and COO⊖K⊕ | |

-continued

| No. | Structure | Common name |
|---|---|---|
| 5 | CF$_3$—⟨phenyl(Cl)⟩—O—⟨phenyl(COOCH$_2$COC$_2$H$_5$, =O)⟩—NO$_2$ | fluoroglycofen |
| 6 | CF$_3$—⟨phenyl(Cl)⟩—O—⟨phenyl(COOCH(CH$_3$)—COC$_2$H$_5$, =O)⟩—NO$_2$ | lactofen |
| 7 | CF$_3$—⟨phenyl(Cl)⟩—O—⟨phenyl(C(=O)—NHSO$_2$CH$_3$)⟩—NO$_2$ | fomesafen |
| 8 | CF$_3$—⟨phenyl(Cl)⟩—O—⟨phenyl(OC$_2$H$_5$)⟩—NO$_2$ | oxyfluorfen |

Some of the diphenyl ethers I are commercially available compounds; others may be prepared in accordance with the abovementioned art.

The diphenyl ether derivatives I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, alkali metal and alkaline earth metal salts of dibutylnaphthalenesulfonic acid, lauryl ether sulfate, fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributyphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient. An agent contains for instance about 10 to 80 wt % of active ingredient, about 30 to 90 wt % of liquid or solid carriers and, if desired, up to 20 wt % of surfactants. If required, the formulation may be diluted down to a suitable use concentration.

Examples of formulations are as follows:

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 3 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight water and finely distributing it therein, an aqueous dispersion is obtained containing 0.02% by weight of the active ingredient.

IV. 20 parts by weight of compound no. 5 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 4 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 5 is intimately mixed with 97 parts by weight of particulate kaolin. A dust is obtained containing 3% by weight of the active ingredient.

VII. 30 parts by weight of compound no. 5 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 5 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

IX. 10 parts by weight of compound no. 1 is well mixed with 4 parts by weight of the sodium salt of diisobutylnaphthalene-alpha-sulfonic acid, 20 parts by weight of the sodium salt of a lignin-sulfonic acid obtained from a sulfite waste liquor, 38 parts by weight of powdered silica gel and 38 parts by weight of kaolin, and triturated in a hammer mill. By uniformly distributing the mixture in 20,000 parts by weight of water, a spray liquor is obtained containing 0.1% by weight of the active ingredient.

The action and speed of action may be promoted for example by additives increasing the efficacy, such as organic solvents, spreader-stickers and oils. This means that the amount of actual active ingredient applied may be decreased. The agents are usually applied to the plants by spraying the foliage—for example by using water as vehicle and employing conventional spraying techniques with spray liquor amounts of from about 100 to 1,000 l/ha. The agents may also be applied in the low-volume and ultra-low-volume methods, and as micro-granules.

The diphenyl ethers I may be applied at rates of from 0.001 to 10, preferably from 0.01 to 3, kg/ha, and particularly from 1 to 1,000 g/ha.

The agents may be employed on their own, or in admixture with other agents or active ingredients. If desired and depending on the purpose intended, other defoliants, desiccants, crop protection agents or pesticides may be added.

It has also been found that mixtures of the diphenyl ethers I for example with active ingredients (A) to (C) below give even better control over undesired resprouting in plants after desiccation or defoliation in cotton. The defoliation effect is retained or even reinforced:

(A) Herbicidally effective active ingredients from the group of a. chloroacetanilides, such as 2-chloro-N-(2,6-dimethylphenyl)-N-(1H-pyrazol-1-ylmethyl)-acetamide disclosed in DE-OS 26 48 008 (common name: metazachlor), b. substituted quinoline-8-carboxylic acids, such as 3,7-dichloroquinoline-8-carboxylic acid disclosed in EP-A-104 389 and 3-methyl-7-chloroquinoline-8-carboxylic acid disclosed in EP-A-60 429, c. cyclohexenone derivatives such as 2[(1-ethoxyimino)-butyl]-5-[2-(ethylthio)-propyl]-3-hydroxy-2-cyclohexen-1-one (common name: sethoxydim) disclosed in DE-OS 28 22 304 and 2-[1-(ethoxyimino)-butyl]-3-hydroxy-5-(2H-tetrahydrothiopyran-3-yl)-2-cyclohexen-1-one (common name: cycloxydim) disclosed in DE-OS 31 21 355, d. phenoxyalkanecarboxylic acids, such as (4-chloro-2-methylphenoxy)-acetic acid, e. 3-(isopropyl)-1H-2,1,3-benzothiadiazin-4(3H)-one-2,2-dioxide, disclosed in DE-OS 15 42 836 (Bentazon®), f. dinitroanilines, such as N-(1-ethylpropyl)-3,4-dimethyl-2,6-dinitroaniline disclosed in DE-OS 22 41 408, g. imidazolinones, e.g., 2-[4,5-dihydro-4-methyl-4-(1-methylethyl)-5-oxo-1H-imidazol-2-yl]-3-quinolinecarboxylic acid (Scepter®), h. 3,4,5,6-tetrahydrophthalimides, such as N-[5-(α-chloroacrylic acid ethyl ester)-4-chlorophenyl]-3,4,5,6-tetrahydrophthalimide disclosed in EP-A No. 0 240 659, i. sulfonylurea derivatives, such as those known under trade names Glean®, Ally®, Express®, Logran®, Setoff®, Muster®, Londax®, Oust®, Classic®, Bacon®, Harmony® or Remedy® for example from DE-A-27 15 786, EP-A-7687, 202 830, 44 808, 44 807, 136 061, 51 566, 7687, 84 020, 30 142, 237 292, 232 067, U.S. Pat. No. 4,547,215 or Chemical Abstracts 102, 220, 905.

Preferred compounds for admixture are:

2-methyl-6-ethyl-ethoxymethyl-2-chloroacetanilide 2-methyl-6-ethyl-N-(methoxy-1-methylethyl)-2-chloroacetanilide 2,6-dimethyl-N-(1-H-pyrazolyl-1-yl-methyl)-2-chloroacetanilide 2,6-diethyl-N-(methoxymethyl)-2-chloroacetanilide 3-methyl-7-chloroquinoline-8-carboxylic acid (salts, esters)

3,7-dichloroquinoline-8-carboxylic acid (salts, esters)

2-[(1-ethoxyimino)butyl]-5-[2-(ethylthio)-propyl]-3-hydroxy-2-cyclohexan-1-one (salts)

2-[(1-trans-chloroallyloxyimino)butyl]-5-[-2-(ethylthio)-propyl]-3-hydroxy-2-cyclohexan-1-one (salts)

2-[(1-trans-chloroallyloximino)propyl]-5-[-2-(ethylthio)-propyl]-3-hydroxy-2-cyclohexan-1-one (salts)

2-[(1-ethoximino)butyl]-5-[-2-H-tetrahydrothiopyran-3-yl]-3-hydroxy-2-cyclohexan-1-one (salts)

2-[(1-ethoximino)propyl]-5-(2,4,6-trimethylphenyl)-3-hydroxy-2-cyclohexan-1-one (salts)

2-methyl-4-chlorophenoxyacetic acid (salts, esters, amides)

2-[2-methyl-4-chlorophenoxy]propionic acid (salts, esters, amides)

4-[2-methyl-4-chlorophenoxy]-butyric acid (salts, esters, amides)

4-[-2,4-dichlorophenoxy]-butyric acid (salts, esters, amides)

2-[-2,4-dichlorophenoxy]-propionic acid (salts, esters, amides)

2,2-dichlorophenoxyacetic acid (salts, esters, amides)

3,5,6-trichloropyridyl-2-oxyacetic acid (salts, esters, amides)
3-(1-methylethyl)-1-H-2,1,3-benzothiadiazin-4-(3H)-one-2,2-dioxide (salts)
3-(1-methylethyl)-1-cyano-2,1,3-benzothiadiazin-4-(3H)-one-2,2-dioxide (salts)
N-(1-ethylpropyl)-3,4-dimethyl-2,6-dinitroaniline
2-[4,5-dihydro-4-methyl-4-(1-methylethyl)-5-oxo-1H-imidazol-2-yl]-3-quinolinecarboxylic acid
N-[5-(α-chloroacrylic acid ethyl ester)-4-chlorphenyl]-3,4,5,6-tetrahydrophthalimide.

(B) Defoliants and desiccants, as mentioned for instance in Cathey, G. W. (1986) Physiology of defoliation in cotton production, in "Cotton Physiology" (J. R. Mauney, J. McD. Stewart, eds.) The Cotton Foundation reference book series, No. 1, Chapter 14, 143–153 and in Morgan, P. W. (1985) Chemical manipulation of abscission and desiccation. In "Agricultural Chemicals of the Future" (J. L. Hilton, ed.) BARC Symposium 8, 61–74. Rowman & Allanheld, Totowa.

a. 6,7-Dihydrodipyridol (1,2-a:2′, 1′-c)pyridilium ion as dibromide monohydrate salt (common name: diquat) and 1,1′-dimethyl-4,4′-bipyridinium ion as dichloride or dimethylsulfate salt (common name: paraquat),
b. (2-chloroethyl)phosphonic acid (Ethrel ®),
c. S,S,S-tributylphosphorotrithioate and S,S,S-tributylphosphorotrithioite,
d. 2,3-dihydro-5,6-dimethyl-1,4-dithiyne-1,1,4,4-tetraoxide (Harvade ®),
e. salts of N-(phosphonomethyl)glycine, such as the isopropyl-ammonium salt (Roundup ®),
f. magnesium and sodium chlorate,
g. 1,2-dihydropyridazine-3,6-dione,
h. 7-oxabicyclo[2,2,1]heptane-2,3-dicarboxylic acid (common name: endothall).

Preferred compounds for admixture are:
2-chloroethylphosphonic acid
S,S,S-tributylphosphorotrithioate and trithioite
2,3-dihydro-5,6-dimethyl-1,4-dithiyne-1,1,4,4-tetraoxide
N-(phosphonomethyl)glycine (salts)
1,2-dihydropyridazine-3,6-dione
perchlorates
7-oxabicyclo[2,2,1]heptane-2,3-dicarboxylic acid (salts, esters, amides)
1,1-ethylene-2,2-bipyridyllum dibromide.

(C) Growth retardants selected from the groups consisting of
a. quaternary ammonium salts from the group of N,N-dimethylazacycloheptanium salts, N,N-dimethylpiperidinium salts, N,N-dimethylhexahydropyridazinium salts, N,N-dimethyltetrahydropyridazinium salts, N-methylpyridinium salts, N,N-dimethylpyrrolidinium salts and N,N,N-trimethyl-N-2-chloroethylammonium salts, especially N-2-chloroethyl-N-trimethylammonium chloride (common name: chlormequat chloride) and N,N-dimethylpiperdinium chloride (common name: mepiquat chloride),
b. pyrimidine compounds as known from U.S. Pat. No. 3,818,009 and Journal of Plant Growth Regulation 7:27, 1988 (e.g., those with the common names ancymidol and flurprimidol),
c. pyridine compounds known from DE-A-30 15 025,
d. Norbornadiazetines as disclosed in DE-OS 26 15 878 and 27 42 034,
e. Growth-regulatory triazole compounds as described in European Application 88104320.2, in British Crop Protection Conference-Weeds 1982, vol. 1, BCPC Publications, Croydon, 1982, p. 3, in Plant Cell Physiol. 25, 611, in Pestic. Sci. 19, 153, in J. Agron. Crop. Sci. 158, 324 or in J. Plant Growth Regul. 4, 181, e.g., 1-phenoxy-3-(1H-1,2,4-triazol-1yl)-4-hydroxy-5,5-di-methylhexane,
f. 2-acyl-3-hydroxycyclohex-2-en-1-ones, as disclosed in EP-A-126 713 and 123 001,
g.
1-(4-chlorophenoxy)-3,3-dimethyl-1-[1,2,4-triazol-1-yl]-butan-2-one (common name: triadimefon)
N [2,4-dimethyl-5-[trifluoromethylsulfonylamino]]-phenyl-acetamide (common name: mefluidide)
2-chloro-2′,6′-diethyl-N-[methoxymethyl]-acetanilide (common name: alachlor)
S-ethyldipropylthiocarbamate (common name: EPTC)
succinic acid-2,2-dimethylhydrazide (common name: daminozid)

Preferred compounds for admixture are:
N,N,N-trimethyl-N-2-chloroethylammonium salts
N,N-dimethylpiperidinium salts
N-methylpyridinium salts
α-cyclopropyl-α-(4-methoxyphenyl)-5-pyrimidine methanol
α-cyclopropyl-α-(4-trifluoromethoxyphenyl)-5-pyrimidine methanol
5(4-chlorophenyl)3,4,5,9,10-pentaaza-tetracyclo[5,4,1,0$^2$, $^6$,O$^8$, $^{11}$]-dodeca-3,9-dione
all-cis-8-(4-chlorophenyl)-3,4,8-triazatetracyclo[4,3,1,0,0$^{2,5}$,0$^{7,9}$]-dec-3-one
succinic acid-mono-N,N-dimethylhydrazide
ethyl N,N-dipropylthiolcarbamate
N-2,4-dimethyl-5-(trifluoromethyl)-sulfonylamino-phenylacetamide
1-(4-chlorophenoxy-)3,3-dimethyl-1-(1,2,4-triazol-1-yl)-2-butanone
2-propylcarbonyl-5-ethoxycarbonyl-3-hydroxy-2-cyclohexen-1-one
1-(1,2,4-triazol-1-yl)-1-methoxy-2-(2,4-dichlorophenyl)-propan-2-ol
2,2-dimethyl-4-(1,2,4-triazol-1-yl)-6-phenoxyhexan-3-ol
2,2-dimethyl-4-(1,2,4-triazol-1-yl)-5-(4-chlorophenyl)-pentan-3-ol
2,2-dimethyl-4-(1,2,4-triazol-1-yl)-5-(4-chlorophenyl)-pent-4-en-1-ol
2,2-dimethyl-4-(1,2,4-triazol-1-yl)-5-cyclohexylpent-4-en-3-ol
1(5-methyl-1,3-dioxan-yl-5)-4-(1,2,4-triazol-1-yl)-4-(4-trifluoromethylphenyl)-propen-2-ol.

USE EXAMPLES

N-Phenyl-N′-(1,2,3-thiadiazol-5-yl)-urea (Droppe ®, common name: thidiazuron) was used as comparative agent A.

The active ingredients were used in the form of formulated commercial products. The figures given for the action relate to the proportion of active ingredient.

The amount of water in the formulations corresponded to 1,000 l/ha.

The test plants were young, 5- to 6-leaved (not including cotyedons) cotton plants of the Stoneville 825 variety, which were grown under greenhouse conditions (relative humidity: 50 to 70%).

USE EXAMPLES 1 AND 2

The leaves of the cotton plants were sprayed to runoff with aqueous formulations (with the addition of 0.15 wt % of the fatty alcohol alkoxylate Plurafac LF 700 ®, based on the spray liquor) of the active ingredients given below. 7 days after application of the active ingredients the number of leaves shed and the degree of defoliation were assessed in %. No leaves were shed from the untreated control plants.

| Agent containing active ingred. no. | Application rate [kg/ha] | Defoliation [%] | Day/night temperature [°C.] |
|---|---|---|---|
| 2 (Blazer ®) | 0.062 | 20 | 20/13 |
| | 0.125 | 78 | |
| | 0.250 | 88 | |
| Comparative agent A | 0.125 | 0 | 20/13 |
| | 0.5 | 6 | |
| 5 (Superblazer ®) | 0.03 | 62 | 21/15 |
| | 0.062 | 83 | |
| Comparative agent A | 0.03 | 6 | 21/15 |
| | 0.062 | 10 | |

The results obtained in Use Example 1 and 2 show that the agents according to the invention lead at low application rates to defoliation of the plants and that they retain their action even at low temperatures. They are significantly superior to comparative agent A.

We claim:
1. A method of effecting desiccation and abscission of plant organs which comprises administering to the plants or their habitats a desiccation- and abscission-effective amount of a compound of the formula:

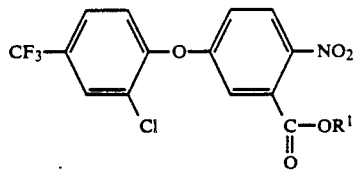

wherein $R^1$ is hydrogen, an alkali metal or alkaline earth metal ion, substituted or unsubstituted ammonium, alkyl of 1 to 4 carbon atoms, or alkoxycarbonylalkyl having a total of 1 to 6 carbon atoms.

2. The method of claim 1 wherein the plant is cotton.
3. The method of claim 1 wherein the amount administered is from 0.001 to 10 kg/ha.